United States Patent [19]
Fukuoka et al.

[11] 3,981,906
[45] Sept. 21, 1976

[54] PROCESS FOR PREPARING ALKYL 4,4'-(ETHYLENEDIOXY)BIS-BENZOATES

[75] Inventors: Yohei Fukuoka, Fuji; Toshio Kato, Kurashiki; Norio Imai, Fuji; Joji Nishikido, Fuji; Masato Hamada, Yokohama; Hiroshi Mikami, Chigasaki; Hirohumi Iwasaki, Moriyama; Toshihisa Koike, Fuji, all of Japan

[73] Assignee: Asahi Kasei Kogyo Kabushiki Kaisha, Osaka, Japan

[22] Filed: May 7, 1975

[21] Appl. No.: 575,229

[30] Foreign Application Priority Data
May 9, 1974    Japan.............................. 49-50713

[52] U.S. Cl............................................. 260/473 R
[51] Int. Cl.²........................................ C07C 69/76
[58] Field of Search ................................. 260/473 R

[56] References Cited
UNITED STATES PATENTS
3,855,274    12/1974    Kato et al. ...................... 260/473 R FOREIGN PATENTS OR APPLICATIONS
1,917,540    11/1969    Germany........................ 260/473 R
2,147,901     4/1973    Germany........................ 260/473 R
45-858       12/1970    Japan............................... 260/473 R Primary Examiner—Paul J. Killos
Attorney, Agent, or Firm—Armstrong, Nikaido & Wegner

[57] ABSTRACT

Alkyl 4,4'-(ethylenedioxy)bis-benzoates having improved properties such as anti-oxidation and anti-coloration are prepared in high yield and selectivity by, at the first step, reacting an excess alkyl p-hydroxybenzoate with a recycling alkyl p-(2-chloro-ethoxy)benzoate with heating in the presence of an alkali carbonate and an inert organic solvent until almost said alkyl p-(2-chloroethoxy)benzoate is consumed to produce an alkyl 4,4'-(ethylenedioxy)bis-benzoate and at the second step adding ethylene dichloride to the reaction system and continuing the heating to produce an alkyl p-(2-chloroethoxy)benzoate which is recycled, and separating the alkyl 4,4'-(ethylenedioxy)bis-benzoate produced.

9 Claims, No Drawings

PROCESS FOR PREPARING ALKYL 4,4'-(ETHYLENEDIOXY)BIS-BENZOATES

This invention relates to a process for preparing an alkyl 4,4'-(ethylenedioxy)bis-benzoate. More particularly, this invention relates to a process for preparing an alkyl 4,4'-(ethylenedioxy)bis-benzoate by reacting an excess alkyl p-hydroxybenzoate with an alkyl p-(2-chloroethoxy)benzoate with heating in the presence of an alkali carbonate at the first step, and then reacting the unreacted alkyl p-hydroxybenzoate with ethylene dichloride with heating to produce an alkyl p-(2-chloroethoxy)benzoate which is recycled.

In order to carry out the above-mentioned etherification industrially, it is desirable to conduct the reaction with great reaction rate and high conversion and selectivity from an economical point of view. Further when an alkyl 4,4'-(ethylenedioxy)bis-benzoate is used as a starting material for producing high polymer materials such as fibers, the one having extremely high purity and having the least coloration with heating is required.

The present inventors had proposed in British Pat. No. 1,331,158 a process for preparing an alkyl 4,4'-(ethylenedioxy)benzoate in excellent yield with a shortened reaction time by recycling an alkyl p-(2-chloroethoxy)benzoate. But said process has various defects to be improved. One of the defects is low selectivity in the etherification. According to said process, an alkyl p-(2-chloroethoxy)benzoate, which is recycled, is reacted with an alkyl p-hydroxybenzoate and ethylene dichloride simultaneously and by-products produced are gradually accumulated in the recycling alkyl p-(2-chloroethoxy)benzoate. The accumulated by-products, by themselves or by bringing about further side reactions, lower the purity and chromaticity of the desired alkyl 4,4'-(ethylenedioxy)bis-benzoate. In order to remove the above-mentioned defect of said process, the recycling alkyl p-(2-chloroethoxy)benzoate may be purified completely by using a highly developed technology, but such a method is greatly disadvantageous from an economical point of view. Another defect of said process is that the conversion of the starting alkyl p-hydroxybenzoate is low and if the convertion of alkyl p-hydroxybenzoate is to be raised, then the selectivity for the desired alkyl 4,4'-(ethylenedioxy)bis-benzoate is lowered.

In order to overcome the defects of the abovementioned process and to provide an economically advantageous process for producing an alkyl 4,4'-(ethylenedioxy) bis-benzoate, it is necessary to increase the reaction rate of the etherification so as to obtain the desired alkyl 4,4'-(ethylenedioxy)bis-benzoate with high conversion and high selectivity within a short reaction time. The present inventors have found that such a great reaction rate can be attained when a specific procedure is employed.

It is an object of the present invention to provide a process for preparing alkyl 4,4'-(ethylenedioxy) bis-benzoates in excellent yield with high selectivity and conversion. It is another object of the present invention to provide a process for preparing alkyl 4,4'-(ethylenedioxy)bis-benzoates having high purity and improved properties against oxidation and coloration. Further objects and advantages of the present invention will be apparent to one skilled in the art from the accompanying disclosure and discussion.

The present invention provides an improved process for preparing alkyl 4,4'-(ethylenedioxy)bis-benzoates which comprises, at the first step, reacting an excess alkyl p-hydroxybenzoate with a recycling alkyl p-(2-chloroethoxy)benzoate with heating in the presence of an alkali carbonate and an inert organic solvent until almost said alkyl p-(2-chloroethoxy)benzoate is consumed to produce an alkyl 4,4'-(ethylenedioxy) bis-benzoate and at the second step, adding ethylene dichloride to the reaction system and continuing heating to produce an alkyl p-(2-chloroethoxy)-benzoate which is recycled.

According to the process of the present invention, the reaction can be carried out with high conversion in a short reaction time and with suppressing relatively side reactions, which not only increases selectivity for the desired product but also improves properties of the desired product such as against oxidation and coloration by heating caused by the by-products.

In the process of the present invention, the use of an excess alkyl p-hydroxybenzoate at the first step makes the acidity of the reaction system stable and also makes the reaction with a thermally unstable alkyl p-(2-chloroethoxy)benzoate rapid, so that the desired alkyl 4,4'-(ethylenedioxy)bis-benzoate can be produced rapidly with excellent selectivity and the decomposition of the alkyl p-(2-chloroethoxy)benzoate in the system can be suppressed to a minimum. Furthermore, since no ethylene dichloride is present in the first step of the reaction unlike the process of British Pat. No. 1,331,158, there is not by-produced hydrogen chloride and vinyl chloride which bring about side reactions.

In the second step of the present reaction, the unreacted alkyl p-hydroxybenzoate is reacted with ethylene dichloride, which is added preferably in excess, with heating to produce an alkyl p-(2-chloroethoxy)benzoate preferentially. The desired alkyl 4,4'-(ethylenedioxy)bis-benzoate present in the reaction system acts as a good solvent for the reaction and suppresses the side reactions of ethylene dichloride. Furthermore, since the reaction system of the second step is relatively weak alkaline, side reactions of ethylene dichloride to hydrochloric acid and vinyl chloride are also suppressed.

According to the process of the present invention, the selectivity for the alkyl 4,4'-(ethylenedioxy)-bis-benzoate is 7–10% or more higher than that of the known method, so that the separation and purification of the desired compound is very easy. This is very advantageous in industrial production.

As the alkyl p-hydroxybenzoate used in the present process the esters of p-hydroxybenzoic acid with lower alcohols such as methanol, ethanol, propanol, and the like, may be used. Particularly, methyl p-hydroxybenzoate is most preferably industrially.

As the alkyl p-(2-chloroethoxy)benzoate, methyl p-(2-chloroethoxy)benzoate, ethyl p-(2-chloroethoxy)benzoate, and the like may be used.

Reaction temperatures of from about 150° to 220°C may preferably be used both in the first step and the second step reactions. The temperature of about 180°C is particularly preferable in the both reactions. The reaction time depends on the temperature employed. If the reaction temperature of 180°C is employed, the reaction time of the first step is preferably 5 to 20 minutes and that of the second step is preferably 10 to 60 minutes.

The molar ratio of the alkyl p-hydroxybenzoate to the alkyl p-(2-chloroethoxy)benzoate in the first step reaction is preferably 1 to 0.3 – 0.8, more preferably 1 to 0.4 – 0.6. If the molar ratio is in the range of 1 to 0.3 – 0.8, the decomposition of the alkyl p-hydroxybenzoate and the alkyl p-(2-chloroethoxy)benzoate is very little, the recycle of the alkyl p-(2-chloroethoxy)benzoate is easy and the conversion of alkyl p-hydroxybenzoate becomes greater.

The molar ratio of ethylene dichloride to the alkyl p-hydroxybenzoate charged in the second step reaction is preferably 0.7 – 2 to 1, more preferably 1 – 1.5 to 1. If the molar ratio of ethylene dichloride to the alkyl p-hydroxybenzoate charged is less than 0.7 to 1, the reaction rate is lowered. If the molar ratio of ethylene dichloride to the alkyl p-hydroxybenzoate charged is more than 2 to 1, the reaction rate is lowered, the by-production of vinyl chloride increases and the decomposed products increase.

As the inert organic solvent, methanol, acetone, acetonitrile, dioxane, dimethylformamide, etc. may be used. Among the solvents, methanol is most preferably to carry out the reaction effectively, easily and economically. The amount of methanol is not limited and is sufficient when it can be used as a solvent. More specifically 1 – 100 moles, preferably 3 – 10 moles of methanol per mole of the alkyl p-hydroxybenzoate may be used. If methanol is used in the range of 1 to 100 moles, the amount of methoxy group-containing products other than the desired compound is very little and by-products are formed in a very little amount. Outside the above range, the reaction rate becomes slow.

As the alkali carbonate, sodium carbonate and potassium carbonate may be used. The amount of the alkali carbonate is not limited but usually is 1.0 to 2.4 moles, preferably 1.4 to 1.8 moles per mole of the alkyl p-hydroxybenzoate. If the amount is less than 1.0 mole, the reaction rate often becomes lowered, and if the amount is more than 2.4 moles, decomposition of the alkyl p-hydroxybenzoate, the alkyl p-(2-chloroethoxy)benzoate, and the like takes place and the coloration of the desired product often increases.

In the application of the present process to industrial production, the alkyl p-(2-chloroethoxy)benzoate recovered from the reaction mixture after the completion of the second step reaction, the amount of the recovered alkyl p-(2-chloroethoxy)benzoate being almost the same as that charged at the beginning of the first step reaction, is reused in the next reaction by recycling. By controlling the reaction conditions such as temperature, time and charging ratio of the starting materials, the alkyl p-(2-chloroethoxy)benzoate can be recovered from the reaction mixture in a constant range without considerable loss or gain compared with the charged amount.

As the method of recycling the recovered alkyl p-(2-chloroethoxy)benzoate, various methods may be used. For example, after completion of the reaction, the alkyl p-(2-chloroethoxy)benzoate may be isolated from the reaction mixture by distillation and be used again as a starting material in the next reaction, or after separating the alkyl 4,4'-(ethylenedioxy)bis-benzoate from the reaction mixture, the alkyl p-(2-chloroethoxy)benzoate in the residual solution may be dehydrated and purified, and if necessary, with further operations such as decoloration, be reused by recycling.

EXAMPLE 1

In a 2 l. autoclave, 365.1 g (2.40 moles) of methyl p-hydroxybenzoate, 205.2 g (0.96 mole) of methyl p-(2-chloroethoxy)benzoate, 203.5 g (1.92 moles) of sodium carbonate and 450 g of methanol were placed and the reaction was carried out with stirring with heating at 180°C for 15 minutes. Then 277.2 g (2.8 moles) of ethylene dichloride was added to the reaction mixture and the heating was continued for additional 30 minutes. After the reaction, 300 ml of methanol was added to the reaction mixture, which was filtered and washed with 300 ml of methanol. The filtered solid was recrystallized from toluene to give 297.1 g of white methyl 4,4'-(ethylenedioxy)bis-benzoate. The filtrate from the reaction mixture was concentrated and then adjusted to pH 3 with concentrated hydrochloric acid and sodium chloride was removed therefrom. The concentrated filtrate was distilled to give a fraction of 140° – 145°C/3 mmHg containing 200.5 g of methyl p-(2-chloroethoxy)benzoate and 62.5 g of methyl p-hydroxybenzoate. The phenol content of the fraction was 0.07% by weight. There was 8 g of methyl 4,4'-(ethylenedioxy)bis-benzoate in the residue of the distillation.

Conversion of methyl p-hydroxybenzoate was 83% and selectivity for methyl 4,4'-(ethylenedioxy)bis-benzoate was 92%. The produced methyl 4,4'-(ethylenedioxy)bis-benzoate had an acid value of 0.1 and a Hazen color number of 10.

The acid value is expressed as the number of moles of the acidic groups in $10^6$ g of the alkyl 4,4'-(ethylenedioxy)bis-benzoate, which is determined by titrating the sample with a caustic alkali in an organic solvent and using thymol blue as an indicator. By the acid value, degree of hydrolysis of the ester groups can be estimated. An acid value of 0.2 or less is preferable in the present invention.

COMPARATIVE EXAMPLE 1

In a 2 l. autoclave, 365.1 g (2.40 moles) of methyl p-hydroxybenzoate, 205.2 g (0.96 mole) of methyl p-(2-chloroethoxy)benzoate, 203.5 g (1.92 moles) of sodium carbonate, 237.5 g (2.40 moles) of ethylene dichloride and 470 g of methanol were placed and the reaction was carried out with stirring with heating at 180°C for 45 minutes. After the reaction, the reaction mixture was treated as described in Example 1 to give 247.3 g of methyl 4,4'-(ethylenedioxy)bis-benzoate. The concentrated filtrate was distilled to give a fraction of 140° – 145°C/3 mmHg containing 198.3 g of methyl p-(2-chloroethoxy)benzoate and 83.6 g of methyl p-hydroxybenzoate. The phenol content in the fraction was 0.13% by weight. Conversion of methyl p-hydroxybenzoate was 77% and selectivity for methyl 4,4'-(ethylenedioxy)bis-benzoate was 83%. The desired product had an acid value of 0.3 and a Hazen color number of 10.

EXAMPLE 2

In a 2 l. autoclave, 365.1 g (2.40 moles) of methyl p-hydroxybenzoate, 256.8 g (1.20 moles) of methyl p-(2-chloroethoxy)benzoate, 203.5 g of sodium carbonate and 480 g of methanol were placed and the reaction was carried out with stirring with heating at 180°C for 20 minutes. Then 308.9 g (3.1 moles) of ethylene dichloride was added to the reaction mixture and the heating was continued for an additional 30 minutes. After the reaction, the reaction mixture was treated as described in Example 1 to give 309.8 g of methyl 4,4'-(ethylenedioxy)bis-benzoate. There were obtained 240.8 g of methyl p-(2-chloroethoxy)benzoate and 47.5 g of methyl p-hydroxybenzoate by distillation. The phenol content in the fraction was 0.09% by weight. There was 11 g of methyl 4,4'-(ethylenedioxy)-bis-benzoate in the residue of the distillation. Conversion of methyl p-hydroxybenzoate was 87% and selectivity for methyl 4,4'-(ethylenedioxy)bis-benzoate was 90%. The desired product had an acid value of 0.2 and a Hazen color number of 10.

COMPARATIVE EXAMPLE 2

In a 2 l. autoclave, 365.1 g of methyl p-hydroxybenzoate, 256.8 g of methyl p-(2-chloroethoxy) benzoate, 203.5 g of sodium carbonate, 237.5 g of ethylene dichloride and 480 g of methanol were placed and the reaction was carried out with stirring with heating at 180°C for 50 minutes. After the reaction, the reaction mixture was treated as described in Example 1 to give 256.6 g of methyl 4,4'-(ethylenedioxy)bis-benzoate. There were obtained 249.8 g of methyl p-(2-chloroethoxy)benzoate and 69.4 g of methyl p-hydroxybenzoate by distillation. The phenol content in the fraction was 0.15% by weight. Conversion of methyl p-hydroxybenzoate was 81% and selectivity for methyl 4,4'-(ethylenedioxy)bis-benzoate was 81%. The desired product had an acid value of 0.3 and a Hazen color number of 20.

EXAMPLE 3

In a 2 l. autoclave, 365.1 g of methyl p-hydroxybenzoate, 205.2 g of methyl p-(2-chloroethoxy)benzoate, 203.5 g of sodium carbonate and 480 g of methanol were placed and the reaction was carried out with stirring with heating at 165°C for 25 minutes. Then 277.2 g of ethylene dichloride was added to the reaction mixture and the heating was continued for additional 50 minutes. After the reaction, the reaction mixture was treated as described in Example 1 to give 297.1 g of methyl 4,4'-(ethylenedioxy)bis-benzoate. There was obtained 201.5 g of methyl p-(2-chloroethoxy)benzoate and 58.4 g of methyl p-hydroxybenzoate by distillation. The phenol content in the fraction was 0.06% by weight. Conversion of methyl p-hydroxybenzoate was 84% and selectivity for methyl 4,4'-(ethylenedioxy)bis-benzoate was 91%. The desired product had an acid value of 0.1 and a Hazen color number of 10.

COMPARATIVE EXAMPLE 3

In a 2 l. autoclave, 365.1 g of methyl p-hydroxybenzoate, 205.2 g of methyl p-(2-chloroethoxy)benzoate, 203.5 g of sodium carbonate, 237.5 g of ethylene dichloride and 480 g of methanol were placed and the reaction was carried out with stirring with heating at 165°C for 75 minutes. After the reaction, the reaction mixture was treated as described in Example 1 to give 245.0 g of methyl 4,4'-(ethylenedioxy)bis-benzoate. There were obtained 196.4 g of methyl p-(2-chloroethoxy)benzoate and 87.6 g of methyl p-hydroxybenzoate by distillation. The phenol content in the fraction was 0.19% by weight. Conversion of methyl p-hydroxybenzoate was 76% and selectivity for methyl 4,4'-(ethylenedioxy)bis-benzoate was 82%. The desired product had an acid value of 0.2 and a Hazen color number of 20.

EXAMPLE 4

In a 2 l. autoclave, 398.7 g (2.40 moles) of ethyl p-hydroxybenzoate, 216.7 g (0.96 mole) of ethyl p-(2-chloroethoxy)benzoate, 203.5 g (1.92 moles) of sodium carbonate and 450 g of methanol were placed and the reaction was carried out with stirring with heating at 180°C for 15 minutes. Then 277.2 g (2.8 moles) of ethylene dichloride was added to the reaction mixture and the heating was continued for additional 30 minutes. After the reaction, 300 ml of methanol was added to the reaction mixture, which was filtered and washed with 300 ml of methanol. The filtered solid was recrystallized from toluene to give 320.5 g of white ethyl 4,4'-(ethylenedioxy)bis-benzoate. The concentrated filtrate was distilled to give a fraction of 150° – 160°C/3 mmHg containing 214.0 g of ethyl p-(2-chloroethoxy)benzoate and 70.2 g of ethyl p-hydroxybenzoate. The phenol content of the fraction was 0.07% by weight. There was 8 g of ethyl 4,4'-(ethylenedioxy)bis-benzoate in the residue of the distillation.

Converstion of ethyl p-hydroxybenzoate was 83% and selectivity for ethyl 4,4'-(ethylenedioxy)bis-benzoate was 91%. The produced ethyl 4,4'-(ethylenedioxy)-bis-benzoate had an acid value of 0.1 and a Hazen color number of 10.

EXAMPLE 5

To the fraction, which was obtained in Example 1, containing 200.5 g of methyl p-(2-chloroethoxy)benzoate and 62.5 g of methyl p-hydroxybenzoate, 302.6 g of methyl p-hydroxybenzoate, the total amount of which was then 365.1 g, 203.5 g of $Na_2CO_3$ and 450 g of methanol were added. The resulting mixture was reacted and treated as described in Example 1 to give 296.5 g of methyl 4,4'-(ethylenedioxy)bis-benzoate. There was obtained a fraction containing 63.5 g of methyl p-hydroxybenzoate. The phenol content of the fraction was 0.05% by weight. There was 6.5 g of methyl 4,4'-(ethylenedioxy)bis-benzoate in the residue of the distillation.

Conversion of methyl p-hydroxybenzoate was 82% and selectivity for methyl 4,4'-(ethylenedioxy)bis-benzoate was 93%. The produced methyl 4,4'-(ethylenedioxy)bis-benzoate had an acid value of 0.1 and a Hazen color number of 10.

As mentioned above, more successful results are obtained in the present process as compared to with the known method. That is, the yield, the conversion, the selectivity, the acid value and the Hazen color number of the process of the present invention are more excellent than those of the known method. Thus the process of the present invention is remarkably effective in industrial production.

What is claimed is:

1. In a process for preparing an alkyl 4,4'-(ethylenedioxy)bis-benzoate comprising reacting an alkyl p-hydroxybenzoate and ethylene dichloride with a recycling alkyl p-(2-chloroethoxy)benzoate in the presence of an alkali carbonate, the improvement which comprises at the first step reacting an excess alkyl p-hydroxybenzoate with an alkyl p-(2-chloroethoxy)benzoate with heating in the presence of an alkali carbonate and an inert organic solvent until almost said alkyl p-(2-chloroethoxy)benzoate is consumed to produce an alkyl 4,4'-(ethylenedioxy)bis-benzoate and at the second step adding ethylene dichloride to the reaction system and continuing the heating to produce an alkyl p-(2-chloroethoxy)benzoate which is recycled.

2. A process according to claim 1, wherein the inert organic solvent is methanol, acetone, acetonitrile, dioxane or dimethylformamide.

3. A process according to claim 1, wherein the inert organic solvent is methanol.

4. A process according to claim 1, wherein the heating is carried out at a temperature of about 150° to 220°C.

5. A process according to claim 1, wherein the heating is carried out at a temperature of about 180°C.

6. A process according to claim 1, wherein 0.3 to 0.8 mole of the alkyl p-(2-chloroethoxy)benzoate is used per mole of the alkyl p-hydroxybenzoate.

7. A process according to claim 1, wherein 0.7 to 2 moles of ethylene dichloride is used per mole of the alkyl p-hydroxybenzoate charged.

8. A process according to claim 1, wherein the alkyl p-hydroxybenzoate is methyl p-hydroxybenzoate and the alkyl p-(2-chloroethoxy)benzoate is methyl p-(2-chloroethoxy)benzoate.

9. A process according to claim 1, wherein the alkali carbonate is sodium carbonate or potassium carbonate.

* * * * *